(12) United States Patent
Weiss et al.

(10) Patent No.: US 7,993,601 B2
(45) Date of Patent: Aug. 9, 2011

(54) DECONTAMINATION UNIT AND PROCESS

(75) Inventors: Richard A. Weiss, Willoughby, OH (US); Michael A. Centanni, Parma, OH (US)

(73) Assignee: STERIS Inc., Temecula, CA (US)

( * ) Notice: Subject to any disclaimer, the term of this patent is extended or adjusted under 35 U.S.C. 154(b) by 357 days.

(21) Appl. No.: 12/033,898

(22) Filed: Feb. 20, 2008

(65) Prior Publication Data
US 2008/0279721 A1 Nov. 13, 2008

Related U.S. Application Data

(60) Provisional application No. 60/893,134, filed on Mar. 6, 2007, provisional application No. 60/962,876, filed on Aug. 1, 2007.

(51) Int. Cl.
A61L 9/00 (2006.01)
B01J 19/00 (2006.01)
B01J 8/02 (2006.01)

(52) U.S. Cl. .................... 422/291; 422/29; 422/211

(58) Field of Classification Search .............. 422/29, 422/211, 291
See application file for complete search history.

(56) References Cited

U.S. PATENT DOCUMENTS

| | | | | |
|---|---|---|---|---|
| 2,348,574 A | 5/1944 | Ross | ................................. | 21/96 |
| 2,404,778 A | 7/1946 | Allison | | |
| 2,823,863 A | 2/1958 | Moyes | .............................. | 237/2 |
| 3,858,645 A | 1/1975 | Egger | ............................... | 165/66 |
| 3,994,684 A | 11/1976 | Tomasulo | ........................... | 21/91 |
| 4,342,200 A | 8/1982 | Lowi, Jr. | | |
| 4,675,923 A | 6/1987 | Ashley | ................................ | 4/599 |
| 4,743,430 A * | 5/1988 | Spielholz | ....................... | 422/133 |
| 4,808,377 A | 2/1989 | Childers et al. | ................. | 422/26 |
| 4,858,256 A | 8/1989 | Shankman | .......................... | 4/597 |
| 4,861,560 A | 8/1989 | Nakajima | ...................... | 422/111 |
| 4,909,988 A | 3/1990 | Childers et al. | ................. | 422/26 |
| 4,987,735 A | 1/1991 | DeLong | ........................ | 60/39.04 |
| 4,993,199 A | 2/1991 | Hughes | ............................ | 51/426 |
| 5,114,670 A | 5/1992 | Duffey | .............................. | 422/24 |
| 5,258,162 A | 11/1993 | Andersson et al. | ............. | 422/28 |
| 5,277,875 A | 1/1994 | Albright et al. | ................ | 422/109 |
| 5,286,447 A | 2/1994 | Fannin et al. | ..................... | 422/28 |
| 5,323,061 A | 6/1994 | Immler et al. | ..................... | 290/2 |
| 5,401,589 A | 3/1995 | Palmer et al. | .................... | 429/13 |
| 5,405,587 A | 4/1995 | Fernandez et al. | ............ | 422/292 |
| 5,472,004 A | 12/1995 | Gilliard | .......................... | 134/111 |

(Continued)

FOREIGN PATENT DOCUMENTS

WO 00/57929 10/2000

(Continued)

OTHER PUBLICATIONS

International Preliminary Report on Patentability, Application No. PCT/US2008/054339, mailed Sep. 17, 2009.

(Continued)

*Primary Examiner* — Kevin Joyner
(74) *Attorney, Agent, or Firm* — Renner, Otto, Boisselle & Sklar, LLP

(57) ABSTRACT

The disclosed invention relates to a decontamination unit which is energy efficient and may be used to decontaminate a large enclosure such as a multi-room building. The invention also relates to a decontamination process. The decontamination unit may be ruggedized for use in hostile environments such as those that may be anticipated for military applications.

30 Claims, 2 Drawing Sheets

U.S. PATENT DOCUMENTS

| | | | |
|---|---|---|---|
| 5,502,975 A | 4/1996 | Brickley et al. | 62/94 |
| 5,520,893 A | 5/1996 | Kasting, Jr. et al. | 422/305 |
| 5,535,944 A | 7/1996 | Knowles | 237/13 |
| 5,634,880 A | 6/1997 | Feldman et al. | 600/132 |
| 5,665,316 A | 9/1997 | Salonia et al. | 422/113 |
| 5,706,846 A | 1/1998 | Sutton | 135/128 |
| 5,868,667 A | 2/1999 | Lin et al. | 600/133 |
| 5,882,590 A | 3/1999 | Stewart et al. | 422/28 |
| 5,916,096 A | 6/1999 | Wiesmann et al. | 52/63 |
| 5,941,672 A | 8/1999 | Lapointe et al. | 414/401 |
| 5,958,336 A | 9/1999 | Duarte | 422/24 |
| 6,077,480 A | 6/2000 | Edwards et al. | 422/28 |
| 6,120,739 A | 9/2000 | Thomas et al. | 422/186.07 |
| 6,199,388 B1 | 3/2001 | Fischer, Jr. | 62/90 |
| 6,279,589 B1 * | 8/2001 | Goodley | 134/102.1 |
| 6,488,902 B1 | 12/2002 | DeCato et al. | 423/210 |
| 6,517,639 B2 | 2/2003 | Toepfer et al. | 134/21 |
| 6,557,365 B2 | 5/2003 | Dinnage et al. | 62/271 |
| 6,645,450 B2 | 11/2003 | Stoltz et al. | 423/245.2 |
| 6,711,907 B2 | 3/2004 | Dinnage et al. | 62/94 |
| 6,734,405 B2 | 5/2004 | Centanni et al. | 219/628 |
| 6,751,964 B2 | 6/2004 | Fischer | 62/94 |
| 6,852,279 B2 | 2/2005 | Williams et al. | 422/4 |
| 6,867,393 B1 | 3/2005 | Lewis | 219/401 |
| 6,906,296 B2 | 6/2005 | Centanni et al. | 219/628 |
| 6,923,716 B2 | 8/2005 | Koeger | 454/230 |
| 6,928,143 B2 | 8/2005 | Menear et al. | 378/69 |
| 6,936,434 B2 | 8/2005 | McDonnell et al. | 435/31 |
| 6,953,549 B2 | 10/2005 | Hill et al. | 422/30 |
| 6,986,386 B2 | 1/2006 | Sekhar et al. | 165/214 |
| 7,040,544 B2 | 5/2006 | Guyer | 237/12.1 |
| 7,047,751 B2 | 5/2006 | Dinnage et al. | 62/94 |
| 7,102,052 B2 | 9/2006 | McVey et al. | 588/303 |
| 7,144,550 B2 | 12/2006 | Devine et al. | 422/28 |
| 7,160,566 B2 | 1/2007 | Fink et al. | 426/235 |
| 7,203,979 B2 | 4/2007 | O'Brien | 4/900 |
| 7,308,798 B2 | 12/2007 | Caggiano | 62/63 |
| 2002/0015672 A1 | 2/2002 | Saint-Martin et al. | 422/295 |
| 2003/0129111 A1 | 7/2003 | Miller et al. | 422/292 |
| 2003/0132100 A1 * | 7/2003 | Crowe et al. | 204/164 |
| 2003/0138347 A1 | 7/2003 | Lin | 422/28 |
| 2003/0164091 A1 | 9/2003 | Hill et al. | 95/90 |
| 2004/0184950 A1 | 9/2004 | McVey et al. | 422/4 |
| 2004/0197252 A1 | 10/2004 | Parrish | 423/235 |
| 2005/0005533 A1 | 1/2005 | Stewart et al. | 52/79.1 |
| 2005/0175500 A1 * | 8/2005 | Adams et al. | 422/29 |
| 2005/0217710 A1 | 10/2005 | Kaipaninen | 134/123 |
| 2005/0220666 A1 | 10/2005 | Foster | 422/28 |
| 2006/0008379 A1 | 1/2006 | Mielnik et al. | 422/32 |
| 2006/0018788 A1 | 1/2006 | Monico et al. | 422/26 |
| 2006/0088441 A1 | 4/2006 | Hill | |
| 2006/0099121 A1 | 5/2006 | Doona et al. | 422/292 |
| 2006/0252974 A1 | 11/2006 | McVey et al. | 588/299 |
| 2006/0270887 A1 | 11/2006 | Watkins | 588/300 |
| 2006/0289490 A1 | 12/2006 | Mielnik | |
| 2007/0098592 A1 | 5/2007 | Buczynski et al. | 422/3 |
| 2007/0274858 A1 | 11/2007 | Childers et al. | 422/28 |

FOREIGN PATENT DOCUMENTS

| | | |
|---|---|---|
| WO | 02/066082 A1 | 8/2002 |
| WO | 02/090747 A2 | 11/2002 |
| WO | 2004110504 | 12/2004 |

OTHER PUBLICATIONS

International Search Report and Written Opinion, Application No. PCT/US2008/054339, mailed Oct. 28, 2008.

* cited by examiner

DECONTAMINATION UNIT AND PROCESS

This application claims benefit under 35 U.S.C. §119(e) to U.S. Provisional Application Ser. No. 60/893,134, filed Mar. 6, 2007, and U.S. Provisional Application Ser. No. 60/962,876, filed Aug. 1, 2007. These applications are incorporated herein by reference in their entireties.

TECHNICAL FIELD

This invention relates to a decontamination unit and to a decontamination process.

BACKGROUND

Decontaminant generating systems, such as those used to generate vaporous hydrogen peroxide (VHP), have been used to decontaminate large enclosures such as rooms and buildings (e.g., hotel rooms, hospital wards, scientific laboratories, etc.) from contaminants such as bacteria, molds, fungi, yeasts, and the like.

SUMMARY

A problem with these decontaminant generating systems is that the electric power requirements tend to be relatively high and consequently these systems are not energy efficient. This invention relates to a decontamination unit that is suitable for decontaminating large enclosures that is energy efficient. This decontamination unit is powered by a relatively small electric generator. The electric generator is powered by an internal combustion engine which generates heat. The heat from the internal combustion engine is used to heat process air. The electric generator provides the required electric power to operate a condensing unit which is used to dehumidify process air. The electric generator is also used to power other equipment in the decontamination unit including blowers, electronic controls, and the like.

With the inventive decontamination unit, the requirement for an electric heater to heat process air has been reduced or eliminated. It may be advantageous to employ a relatively small electric heater for start-up when the decontamination unit is used in relatively cold environments. However, with the inventive decontamination unit, the requirements for electric power are significantly reduced as compared to the prior art. For example, in one embodiment, it may be possible to employ a 30 to 150 kilovolt-ampere (kVA) electric generator using the inventive decontamination unit wherein the internal combustion engine generates heat for heating process air, while the same decontamination unit employing an electric heater for heating process air may require a 200 kVA electric generator. The inventive decontamination unit may be fuel efficient as compared to the prior art due to the fact that the electric generator is reduced in size and as a result the power required from the internal combustion engine to drive the electric generator is reduced in size.

This invention relates to a decontamination unit, comprising: an internal combustion engine, the internal combustion engine adapted to be cooled using a coolant; an electric generator, the electric generator adapted to be powered by the internal combustion engine; a heat recovery coil, the heat recovery coil adapted to receive coolant flowing from the internal combustion engine; an evaporator coil, the evaporator coil being part of a condensing unit, the condensing unit adapted to be powered by the electric generator; a blower, the blower adapted to be powered by the electric generator, the blower being suitable for forcing the flow of process air past the evaporator coil and the heat recovery coil, the evaporator coil being adapted for dehumidifying the process air, the heat recovery coil being adapted for heating the process air; and at least one decontaminant dispersing module suitable for mixing decontaminant with the process air and dispersing the resulting decontaminant air mixture in an area to be decontaminated.

This invention relates to a decontamination process, comprising: operating an internal combustion engine, the internal combustion engine providing power to an electric generator, the internal combustion engine generating heat and being cooled using a coolant; flowing process air containing water vapor past an evaporator coil to condense water vapor and separate it from the process air, the evaporator coil being part of a condensing unit, the electric generator providing power to operate the condensing unit; flowing coolant from the internal combustion engine to a heat recovery coil; flowing the process air from the evaporator coil past the heat recovery coil to heat the process air; mixing the process air with a decontaminant to form a decontaminant air mixture; flowing the decontaminant air mixture in an enclosure to be decontaminated.

BRIEF DESCRIPTION OF THE DRAWINGS

In the annexed drawings all parts and features have like references. A number of the annexed drawings are schematic illustrations which are not necessarily proportioned accurately or drawn to scale.

DETAILED DESCRIPTION

Figure 1:
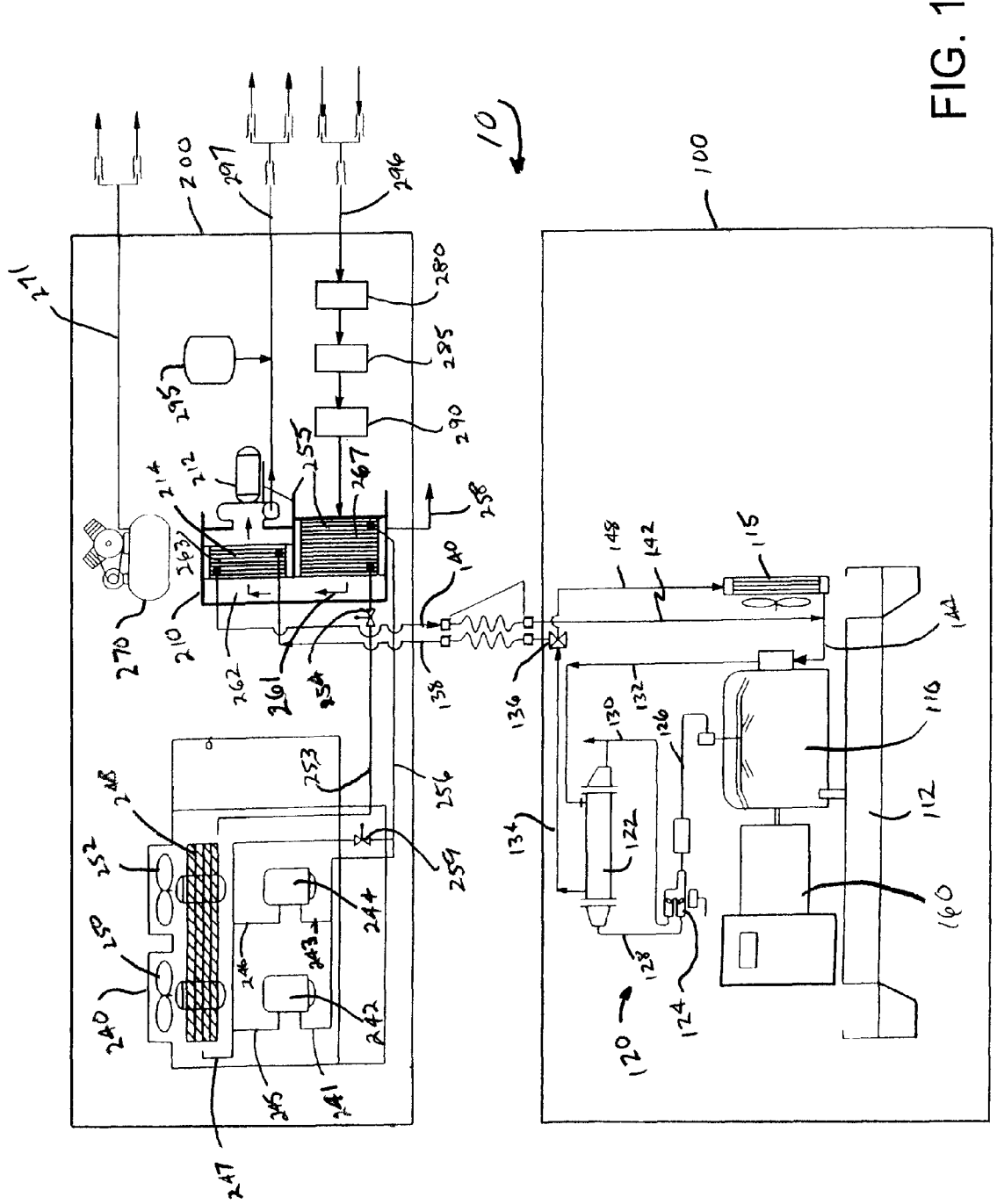
FIG. 1 is a schematic illustration of a decontamination unit within the scope of the present invention.

All ranges and ratio limits disclosed in the specification and claims may be combined in any manner. It is to be understood that unless specifically stated otherwise, references to "a", "an", and/or "the" may include one or more than one, and that reference to an item in the singular may also include the item in the plural. All combinations specified in the claims may be combined in any manner.

The term "ruggedized," and like terms such as "ruggedization," are used herein to refer to apparatus that is: (1) hardened to ensure that five exposures to chemical, biological, radiological or nuclear (CBRN) contaminants, decontaminants and decontaminating procedures over a thirty-day period do not cause the apparatus to require corrective maintenance during that thirty-day period; (2) capable of being used at temperatures ranging from about −32° C. to about 49° C.; (3) capable of being used in relative humidities ranging from about 5% to about 100%; and/or (4) capable of operating when exposed to conventional hazards of solar radiation, rain, fungus, salt fog, sand, dust, vibration and/or shock in accordance with Military Standard 810 (MIL-STD-810).

The term "line" when referring to the drawings may refer to any conduit for conveying a fluid. The conduit may be in any desired form, for example, one or more pipes, tubings, channels, and the like. These may be made of materials sufficient to provide the required properties of strength, flexibility, and resistance to the fluids being conveyed. The lines may be ruggedized to permit use in hostile environments such as those that may be encountered in military applications.

The term "fluid" may refer to a liquid, gas, or mixture thereof.

Figure 2:
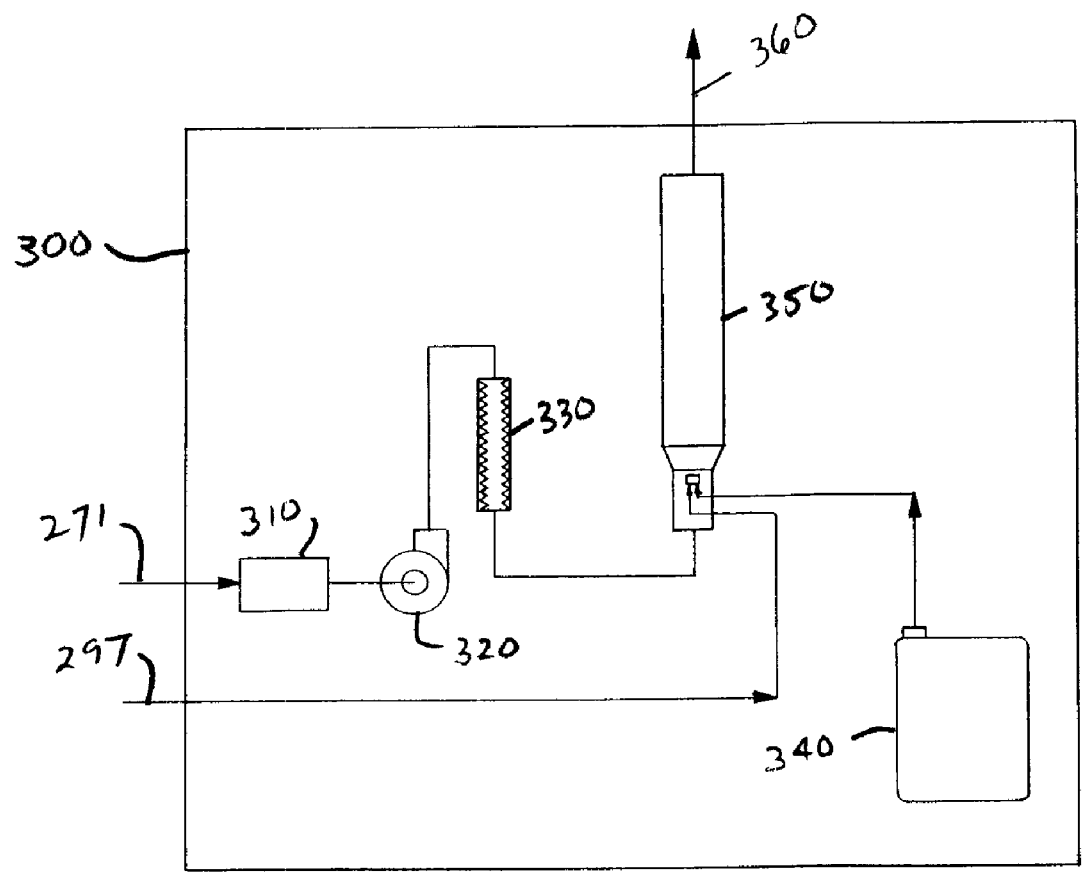
FIG. 2 is a schematic illustration of a decontaminant dispersing module which may be used with the decontamination unit illustrated in FIG. 1.

The inventive decontamination unit, in its illustrated embodiment, will be described with reference to FIGS. 1 and 2. Referring to these figures, decontamination unit 10 comprises power generating unit 100, air handling unit 200, and one or more decontaminant dispersing modules 300. The decontamination unit 10 may be suitable for decontaminating a large enclosure such as a building with an internal volume of any size, for example, in the range from about 10 to about 10,000 cubic meters or more, and in one embodiment in the range from about 50 to about 10,000 cubic meters, and in one embodiment in the range from about 100 to about 5,000 cubic meters, and in one embodiment in the range from about 200 to about 2,500 cubic meters. The enclosure may comprise a single room facility such as a warehouse, theatre, airplane hanger or sports arena, or a multi-room facility such as an office building, school building or hospital. The enclosure to be decontaminated may comprise an aircraft hanger containing one or more aircraft wherein the interior of the hanger as well as the interior and exterior of each aircraft may be decontaminated simultaneously by placing decontaminant dispersing modules in each of the areas to be decontaminated. The multi-room facility may comprise any desired number of separate rooms, for example, the multi-room facility may comprise from 2 to about 1000 rooms, and in one embodiment from 2 to about 500 rooms, and in one embodiment from 2 to about 250 rooms, and in one embodiment from 2 to about 100 rooms, and in one embodiment from 2 to about 50 rooms, and in one embodiment from 2 to about 25 rooms, and in one embodiment from 2 to about 10 rooms, and in one embodiment from 2 to about 5 rooms. Each room may comprise an enclosure with an internal volume of any size, for example, each room may have an internal volume in the range from about 5 to about 1000 cubic meters, and in one embodiment from about 10 to about 500 cubic meters, and in one embodiment from about 10 to about 250 cubic meters, and in one embodiment from about 10 to about 100 cubic meters, and in one embodiment from about 10 to about 50 cubic meters, and in one embodiment from about 10 to about 25 cubic meters. Various deployment options for the decontaminant dispersing modules 300 may be employed. For example, 2 large modules may be deployed, or 10 small modules in combination with 1 large module may be deployed, or 20 small modules may be deployed.

The decontamination unit 10 may be transported using conventional techniques, for example, the decontamination unit 10 may be transported using an airplane, ship, railroad car, truck, and the like. The power generating unit 100 and the air handling unit 200 may be positioned outside the enclosure to be decontaminated, and one or more of the decontaminant dispersing modules 300 may be placed inside the enclosure to be decontaminated. For a multi-room facility, one or more of the decontaminant dispersing modules may be placed in each room.

The decontamination unit 10 may be used in hostile environments such as those that may be anticipated for military applications or for combating terror. When intended for use in such hostile environments the decontamination unit 10, or at least part thereof, may be ruggedized. The decontamination unit 10 may be constructed using any material that is sufficient to provide the apparatus with the required properties of strength and ruggedization. This may include resistance to anticipated operating conditions and hazards, including hot and cold temperatures, exposure to solar radiation, rain, fungus, salt fog, sand, dust, vibration and/or shock, as well as exposure to CBRN contaminants. The decontamination unit 10 may be constructed of materials capable of withstanding exposure to decontaminants that may be used in the decontamination unit 10 and the contaminants likely to be encountered. The materials of construction may include stainless steel, coated steel, aluminum, anodized aluminum, and the like. Various metal alloys may be used, including the stainless steel alloys SS304 and SS316, and aluminum alloy 6061. Non-reactive materials, such as polytheylene, polyvinyl chloride, fluorinated polymers such as polytetrafluorethylene, and the like, may be used.

The power generating unit 100 may comprise internal combustion engine 110 and electric generator 160. The air handling unit 200 may comprise air dehumidifying and heating unit 210, condensing unit 240, compressor 270, high efficiency particle air (HEPA) filter 280, catalytic converter 285, carbon filter 290, and alkaline gas container 295. Each of the decontaminant dispersing modules 300 may comprise a damper 310, blower 320, heater 330, liquid decontaminant container 340, and vaporization chamber 350.

The decontamination unit 10 may be energy efficient and self-contained. The energy efficiency provided by the decontamination unit 10 may relate to using heat generated by the internal combustion engine 110 for heating process air in the air dehumidifying and heating unit 210. The decontamination unit 10 may be self-contained due to the fact that all of the power required to operate the decontamination unit 10 may be provided by the internal combustion engine 110 and the electric generator 160.

The internal combustion engine 110 may comprise any internal combustion engine that is suitable for providing sufficient power to operate the electric generator 160. The internal combustion engine 110 may be ruggedized to permit use in hostile environments that may be anticipated for military applications. The internal combustion engine 110 may be operated using diesel fuel, gasoline, petroleum gas, propane gas, natural gas, liquefied petroleum gas, hydrogen gas, biofuels (e.g., ethanol, biodiesel fuel, etc.), and the like. The internal combustion engine 110 may comprise a spark ignition engine or a compression ignition engine. The internal combustion engine 210 may comprise a two-cycle engine, four-cycle engine, rotary engine, or gas turbine engine. The internal combustion engine may comprise from 1 to about 12 cylinders, and in one embodiment from about 3 to about 8 cylinders. The internal combustion engine 110 may be turbocharged. The internal combustion engine 110 may have an engine capacity in the range from about 1 to about 5 liters, and horsepower in the range from about 5 to about 125. The fuel tank 112 may have a capacity in the range from about 20 to about 180 liters, and in one embodiment from about 50 to about 120 liters. The fuel tank 112 may be a base mounted fuel tank, that is, it may be positioned at the base of or under the internal combustion engine 110.

The electric generator 160 may comprise any electric generator that can be powered by the internal combustion engine 110 and provide sufficient power to operate the various electrically powered components of the decontamination unit 10. These may include blowers 212 and 320, condensing unit 240, compressor 270, heater 330, as well as any lighting, electrically operated valves, computers, monitors, controllers, recorders, and the like, that may be required. The electric generator 160 may be ruggedized to permit use in hostile environments such as those that may be anticipated for military applications. The electric generator 160 may have a power rating in the range from about 30 to about 150 kVA, and in one embodiment in the range from about 60 to about 90 kVA, and in one embodiment in the range from about 70 to about 80 kVA. The power rating is significantly less than that of an electrical generator of about 200 kVA that might be required for a comparably sized decontamination unit wherein the process air is heated using an electric heater powered by the electric generator rather than by heat generated by the internal combustion engine as with the inventive decontamination unit 10.

The internal combustion engine 110 and the electric generator 160 may be combined as a single piece of equipment. This combination may be referred to as a power generator. An example of a power generator that may be used is a 75 kW packaged diesel generator set available from John Deere under the trade designation SKU 553465, Model MJ75UL-2SAE. The engine is a diesel engine. The electric generator may have an output of 75 kVA at 50 Hz. This power generator may be skid mounted and have the dimensions of 80 inches (203 cm) by 40 inches (102 cm) by 52 inches (132 cm), and a weight of 2337 pounds (1060 kg). Additional information concerning this power generator may be found at http://www.gopower.com/products/2097//75-kW-John-Deere-Open-Fully-Packaged-Diesel-Generator-Set-*UL*-(75-KVA-at-50-hz).

The internal combustion engine 110 may include fuel tank 112, radiator 115 and exhaust gas system 120. The exhaust gas system 120 may include exhaust gas heat exchanger 122 and exhaust gas diverter valve 124. Exhaust gas produced by the internal combustion engine 110 may flow through line 126 and exhaust gas diverter valve 124. From exhaust gas diverter valve 124, the exhaust gas may flow through line 128 to and through exhaust gas heat exchanger 122, and from the exhaust gas heat exchanger 122 to the atmosphere. Alternatively, the exhaust gas may bypass exhaust gas heat exchanger 122 and flow from exhaust gas diverter valve 124 through line 130 to the atmosphere. Alternatively, part of the exhaust gas may flow through the exhaust gas heat exchanger 122 and part of the exhaust gas may bypass the exhaust gas heat exchanger 122. The exhaust gas heat exchanger 122 may be used to heat engine coolant flowing from the internal combustion engine 110 to the heat recovery coil 214.

Engine coolant may circulate in the internal combustion engine 110 during its operation in order to control the internal temperature of the internal combustion engine. Any coolant known for use with internal combustion engines may be used. For example, the coolant may comprise a mixture of water and an antifreeze such as ethylene glycol, diethylene glycol, propylene glycol, or a mixture of two or more thereof. The engine coolant may flow from internal combustion engine 110 through line 132 to and through exhaust gas heat exchanger 122. In exhaust gas heat exchanger 122, the coolant may be heated by the exhaust gas. The coolant may flow from exhaust gas heat exchanger 122 through line 134 to three-way valve 136. The coolant may flow through three-way valve 136 to line 138, through line 138 to heat recovery coil 214, through the heat recovery coil 214, and then back to the internal combustion engine 110 through lines 140, 142 and 144. Alternatively, the engine coolant may bypass the heat recovery coil 214 and flow through three-way valve 136 to line 148, through line 148 to radiator 115, through radiator 115 to line 144, and through line 144 back to the internal combustion engine 110. Alternatively, part of the engine coolant may flow through the heat recovery coil 214 and part of the coolant may bypass the heat recovery coil 214. The amount of coolant that flows from the internal combustion engine 110 to the heat recovery coil 214 may depend upon the heating requirements for the heat recovery coil 214. During start up, it may be advantageous to bypass the heat recovery coil 214 and circulate the coolant through the radiator 115 until heat for the process air using the heat recovery coil 214 is needed.

The condensing unit 240, which includes evaporator coil 242 may be used to dehumidify process air flowing through the air dehumidifying and heating unit 210. The condensing unit 240 may comprise any condenser that employs a vapor compression refrigeration system suitable for providing sufficient cooling to the evaporator coil 242 to dehumidify the process air. The condensing unit 240 includes compressors 244 and 246, condensing coil 248, fans 250 and 252, and expansion valve 254. The compressors 244 and 246, and the fans 250 and 252 may be powered using the electric generator 160. The compressors 244 and 246 may be compressors of any suitable design. These may include reciprocating compressors, rotary screw compressors, centrifugal compressors, scroll compressors, and the like. The condensing unit 240 may have a weight in the range from about 1500 to about 4000 pounds (680 to 1814 Kg), and in one embodiment in the range from about 2000 to about 3000 pounds (907 to 1361 Kg), and in one embodiment about 2400 pounds (1089 Kg). The condensing unit 240 may be ruggedized to permit use in hostile environments such as those that may be anticipated for military applications.

The vapor compression refrigeration system used in the condensing unit 240 may involve the use of a refrigerant, which, in the form of a saturated vapor, enters the compressors 242 and 244 from lines 241 and 243, respectively. The refrigerant is compressed in the compressors 242 and 244 to form a high-temperature, high-pressure vapor. The high-temperature, high-pressure vapor flows from the compressors 242 and 244 through lines 245 and 247, and lines 246 and 247, respectively, to the condensing coil 248. In the condensing coil 248, heat is removed from the refrigerant and the refrigerant is condensed to form a saturated liquid. Air that is cooler than the condensing coil 248 is forced across the condensing coil 248 by fans 250 and 252. The refrigerant flows from the condensing coil 248 through line 253 to and through expansion valve 254 where it undergoes a reduction in pressure. This results in an evaporation of part of the liquid refrigerant and a cooling of the refrigerant. A liquid-vapor refrigerant mixture is formed. The liquid-vapor refrigerant mixture flows from the expansion valve 254 through the evaporator coil 255. In the evaporator coil 255, the refrigerant absorbs heat energy from process air flowing across the evaporator coil 255, as indicated by arrow 261. This results in the liquid part of the liquid-vapor refrigerant mixture evaporating and the formation of a saturated vapor in the evaporator coil 255. Moisture from the process air condenses on the exterior of the evaporator coil 255. The resulting condensate flows from the exterior of the evaporator coil 255 out of the air dehumidifying and heating unit 210 as indicated by arrow 258. To complete the refrigeration cycle, the saturated refrigerant vapor flows from the evaporator coil 255 through line 256 to and through lines 241 and 243 back to the compressors 242 and 244. Valve 259 is provided in lines 256 to permit a partial or complete bypass of the compressors 242 and 244. This may be useful during start up or shut down.

The cooling capacity of the refrigeration system used in the condensing unit 240 may be in the range from about 5 to about 25 tons of refrigeration, and in one embodiment in the range from about 15 to about 25 tons of refrigeration, and in one embodiment about 21 tons of refrigeration. The term "ton of refrigeration" refers to the rate of heat removal required to freeze 1 ton (2000 pounds) of water at 32° F. (0° C.) in 24 hours. One ton of refrigeration=12,000 Btu/hr=12,660 kJ/h=3.517 kW.

The refrigerant may comprise any refrigerant suitable for use in a vapor compression refrigeration system. The refrigerant may comprise nitrogen, ammonia, carbon dioxide, one or more organic compounds containing 1 to about 5 carbon atoms (e.g., methylenechloride), one or more hydrocarbons containing 1 to about 5 carbon atoms (e.g., methane, ethane, ethylene, propane, butane, pentane, etc.), or a mixture of two or more thereof. The refrigerant may comprise one or more chlorofluorocarbons or hydrochlorofluorcarbons available from DuPont under the tradename Freon. Examples may include Freon-11 (trichlorofluoromethane), Freon-12 (dichlorodiflouromethane), or a mixture thereof.

Process air flows from the enclosure being decontaminated and enters the air handling unit 200 from gas return line 296 and flows through the HEPA filter 280, catalytic converter 285 and carbon filter 290 prior to entering the air dehumidifying and heating unit 210. The catalytic converter 285 may be used to destroy residual amounts of the decontaminant that may be in the gaseous air stream. For example, the catalytic converter 285 may be use to convert residual hydrogen peroxide to water vapor and oxygen. The catalyst may comprise any transition metal, transition metal oxide, or combination thereof, having the desired catalytic properties. The catalyst may comprise Ag, Mn, Pd, Pt, Rh, an oxide of one or more of the foregoing metals, or a mixture of two or more of the foregoing metals and/or oxides. The catalyst may be supported by a suitable support such as an alumina support. The catalyst may comprise silver in the form of a screen or screen plating. The catalyst may comprise a silver based alloy. The catalyst may comprise manganese dioxide. The catalyst may be in the form of a bed of particulate solids. The process air may flow through a dehumidifying section 267 of the air dehumidifying and heating unit 210 in contact with evaporator coil 255 where it may be dehumidified. Water vapor in the process air may condense out when the air contacts the evaporator coil 255 as discussed above. The dehumidified process air may flow through channel 262 to air heating section 263 of the air dehumidifying and heating unit 210 where it may contact heat recovery coil 214 and be heated. The heated process air may flow through line 297 to the one or more decontaminant dispersing modules 300 where it may be mixed with one or more decontaminants to form a decontaminant air mixture. Optionally, an alkaline gas such as ammonia may flow from alkaline gas container 295, which may be a pressurized cartridge, to line 297 where it may be combined with the process air.

The process air flows from line 297 to each of the decontaminant dispersing modules 300. In each of the modules 300, the process air flows through damper 310 to and through blower 320, then from blower 320 through heater 330 to vaporization chamber 350. The decontaminant (e.g., hydrogen peroxide), which is in liquid form, is stored in liquid decontaminant container 340. The liquid decontaminant flows into vaporizer 350 where it is combined with the process air and vaporized. Compressed air from compressor 270 flows through line 271 to vaporization chamber 350 where it is used to disperse the liquid decontaminant in the process air to form the decontaminant air mixture. The resulting decontaminant air mixture flows out of the vaporization chamber 350, as indicated by arrow 360, into the enclosure to be decontaminated. The damper 310 may be used to control the flow of process air into the decontaminant dispersing module 300. When more than one module is being used, process air may flow to some of the modules but be cut off from other modules as required. Each of the modules 300 may be controlled from a central location.

The decontaminant may comprise one or more oxidants such as peracids (e.g., peracetic acid) and/or peroxides (e.g., hydrogen peroxide), and the like. Oxidants such as hypochlorites, ozone, and the like, may be used. Mixtures of two or more of these may be used. Aqueous solutions of these oxidants may be used. The decontaminant may be combined with a solvent. The solvent may be miscible with water. When the decontaminant comprises hydrogen peroxide, the solvent may be used to enhance the solubility of the hydrogen peroxide and its associated decomposition products in the contaminant and thereby enhance the rate of destruction of the contaminant. The solvent may comprise a mixture of water and tert-butyl alcohol; water and acetonitrile; or water, acetonitrile and isopropyl alcohol. Other suitable solvents may include tetrahydrofuran, dimethylsulfoxide, acetone, acetaldehyde, propylene oxide, acetamide, diethylamine, dimethoxyethane, or a mixture of two or more thereof. The solvent concentration in the combined mixture of decontaminant and solvent may be in the range up to about 60% by weight solvent, and in one embodiment in the range from about 20 to about 60% by weight solvent. The decontaminant may be combined with an alkaline gas such as ammonia in applications wherein an increase in the pH of the decontaminant may be desired.

Vaporous hydrogen peroxide (VHP), which may be generated from an aqueous solution of hydrogen peroxide, may be used as the decontaminant. The aqueous solution may comprise from about 30% to about 40% by weight hydrogen peroxide, and from about 60% to about 70% by weight water. By adding an alkaline gas that is soluble in the hydrogen peroxide (ammonia, for example), the pH of the decontaminant may be controlled. The presence of hydrogen peroxide in the decontaminant may serve to lower the pH (35% aqueous hydrogen peroxide solution has a pH of about 3 to about 4) and the ammonia may be added to raise the pH to a value of about 8 to about 9. The volumetric ratio of VHP to ammonia gas may be in the range from about 1:1 to about 1:0.0001.

VHP, when used in combination with ammonia gas, may be referred to as modified VHP or mVHP. VHP and/or mVHP may be effective microbial and chemical decontaminants because they may provide a broad spectrum of activity against a wide variety of pathogenic microorganisms and chemical pathogenic agents, such as hard to destroy spores of *Bacillus stearothermophilus, Bacillus anthracis*, smallpox virus, and the like. They may be also effective at or close to room temperature (e.g., about 15 to about 30° C.), making them suitable for use in the enclosure to be decontaminated with little or no heating. VHP and/or mVHP may have good material compatibility, rendering them safe for use with a variety of equipment and materials, including electronic equipment, soft furnishings, brass and chrome fixtures, and the like. VHP may degrade to water and oxygen over time, which may not be harmful to a person subsequently entering the decontaminated enclosure. Low levels of hydrogen peroxide (for example, about 1 ppm, or less) that may remain in the decontaminated enclosure may not be considered to pose a risk to a person entering the enclosure.

When the decontaminant air stream flows into the enclosure to be decontaminated and contacts contaminated surfaces to be decontaminated, the process may be regarded as a dry process characterized by the absence of condensate formation on the surfaces being decontaminated. Alternatively, the process may be regarded as a wet process characterized by the formation of a condensate in the form of a liquid film on the surfaces being decontaminated. The liquid film may have a film layer thickness in the range up to about 20 microns, and in one embodiment up to about 10 microns, and in one embodiment up to about 5 microns, and in one embodiment up to about 1 micron. The film layer may be referred to as a microcondensate layer of hydrogen peroxide.

The progress of the decontamination process may be monitored using one or more decontamination or sterilization indicators. These indicators may contain a biological indicator. The biological indicator may comprise one or more test organisms which may be more resistant to the decontamination process than the organisms to be destroyed by the decontamination process. The test organism may be placed in contact with an incubation medium to determine whether the decontamination process was effective.

The temperature of the decontaminant air stream entering the enclosure to be decontaminated may be in the range from about 10° C. to about 50° C., and in one embodiment in the range from about 15° C. to about 50° C., and in one embodiment in the range from about 15° C. to about 30° C. The relative humidity of the decontaminant air stream entering the enclosure to be decontaminated may be in the range from about 0 to about 50%, and in one embodiment in the range from about 20 to about 40% by volume. The term "relative humidity" is used herein to refer to the ratio of the partial pressure of water vapor in the decontaminant air stream to the saturated vapor pressure of water at the temperature of the decontaminant air stream expressed in terms of percentage. The concentration of decontaminant in the decontaminant air mixture entering the enclosure to be decontaminated may be in the range from about 0.01 to about 2% by volume, and in one embodiment in the range from about 0.01 to about 1.5% by volume, and in one embodiment in the range from about 0.01 to about 1% by volume, and in one embodiment in the range from about 0.01 to about 0.5% by volume, and in one embodiment in the range from about 0.02 to about 0.2% by volume, and in one embodiment in the range from about 0.02 to about 0.05% by volume. When the decontaminant comprises solvent, the concentration of decontaminant plus solvent in the decontaminant air mixture entering the enclosure to be decontaminated may be in the range from about 0.01 to about 0.2% by volume, and in one embodiment in the range from about 0.02 to about 0.08% by volume. When the decontaminant comprises an alkaline gas, the concentration of alkaline gas in the decontaminant air mixture entering the enclosure to be decontaminated may be in the range from about 0.001 to about 0.01% by volume, and in one embodiment in the range from about 0.003 to about 0.005% by volume. The gas flow rate through the enclosure being decontaminated may be in the range from about 5 to about 40 cubic feet per minute (CFM) (0.14 to 1.13 cubic meters per minute (CMM)), and in one embodiment in the range from about 10 to about 20 CFM (0.28 to 0.57 CMM). The temperature within the enclosure being decontaminated may be in the range from about 10° C. to about 50° C., and in one embodiment in the range from about 15° C. to about 50° C., and in one embodiment in the range from about 15° C. to about 30° C. The operating pressure within the enclosure being decontaminated may be slightly negative to prevent the leakage of contaminants and decontaminants from the enclosure. The internal pressure may be in the range of up to about 10 inches of water below atmospheric pressure, and in one embodiment in the range from about 0.01 to about 5 inches of water, and in one embodiment in the range from about 0.01 to about 2 inches of water, and in one embodiment in the range from about 0.01 to about 1 inch of water, and in one embodiment in the range from about 0.01 to about 0.5 inch of water, and in one embodiment in the range from about 0.01 to about 0.3 inch of water below atmospheric pressure.

The contaminants may comprise one or more chemical, biological, radiological and/or nuclear (CBRN) warfare agents. Different levels of decontamination may be accomplished within the enclosure to be decontaminated. As used herein, the term "decontamination," is intended to encompass both microbial decontamination as well as chemical decontamination—the destruction of chemical agents, or their conversion to harmless or odorless compounds. Decontamination may also encompass the neutralizing of unpleasant odors, such as tobacco smoke, perfume, or body odor residues, and odors and dampness due to molds. "Microbial decontamination" may be used herein to encompass the destruction of biological contaminants, specifically, living microorganisms, and also the destruction or inactivation of pathogenic forms of proteinaceous-infectious agents (prions). The term microbial decontamination encompasses sterilization, the highest level of biological contamination control, which connotes the destruction of all living microorganisms. The term also includes disinfection, the destruction of harmful microorganisms, and sanitizing, which connotes being free from germs. "Chemical decontamination" is intended to encompass the destruction of pathogenic chemical agents or their conversion to less harmful or odiferous species.

Exemplary biological contaminants which may be destroyed in the decontamination process include bacterial spores, vegetative bacteria, viruses, molds, and fungi. Some of these may be capable of killing or causing severe injury to mammals, particularly humans. Included among these are viruses, such as *equine encephalomyelitis* and smallpox, the coronavirus responsible for Severe Acute Respiratory Syndrome (SARS); bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

Also included are the less harmful microorganisms, such as those responsible for the common cold (rhinoviruses), influenza (orthomyxoviruses), skin abscesses, toxic shock syndrome (*Staphylococcus aureus*), bacterial pneumonia (*Streptococcus pneumoniae*), stomach upsets (*Escherichia coli*, Salmonella), and the like.

Exemplary pathogenic chemical agents may include substances which are often referred to as chemical warfare agents, such as poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation.

Exemplary chemical pathogenic agents may include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl) sulfide (mustard gas or "HD") and dichloro(2-chlorovinyl)arsine (Lewisite); nerve agents, such as ethyl-N, N dimethyl phosphoramino cyanidate (Tabun or agent GA), o-ethyl-S-(2-diisopropyl aminoethyl) methyl phosphono-thiolate (agent VX), isopropyl methyl phosphonofluoridate (Sarin or Agent GB), methylphosphonofluoridic acid 1,2,2-trimethylpropyl ester (Soman or Agent GD).

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:

1. A decontamination unit, comprising:
a power generating unit comprising:
an internal combustion engine, the internal combustion engine adapted to be cooled using a coolant; and
an electric generator, the electric generator adapted to be powered by the internal combustion engine, the internal combustion engine and electric generator positioned in the power generating unit;
an air handling unit comprising:
a heat recovery coil, the heat recovery coil adapted to receive coolant flowing from the internal combustion engine;
an evaporator coil, the evaporator coil being part of a condensing unit, the condensing unit adapted to be powered by the electric generator; and
a blower, the blower adapted to be powered by the electric generator, the blower being suitable for forcing a flow of process air past the evaporator coil and the heat recovery coil, the evaporator coil being adapted for dehumidifying the process air, the heat recovery coil being adapted for heating the process air, the heat recovery coil, evaporator coil and blower positioned in the air handling unit; and
at least one decontaminant dispersing module suitable for mixing decontaminant with the process air and dispersing the resulting decontaminant air mixture in an area to be decontaminated.

2. The decontamination unit of claim 1 wherein the decontamination unit further comprises at least one gas process line for flowing gas from the air handling unit to the decontaminant dispersing module.

3. The decontamination unit of claim 1 wherein the decontamination unit further comprises at least one gas return line for flowing gas from the area to be decontaminated to the air handling unit.

4. The decontamination unit of claim 1 wherein the decontamination unit further comprises a compressor positioned in the air handling unit and at least one compressed air line connecting the compressor to the decontaminant dispersing module.

5. The decontamination unit of claim 1 wherein the decontamination unit further comprises a high efficiency particle air filter, catalytic converter and carbon filter positioned in the air handling unit.

6. The decontamination unit of claim 1 wherein the decontaminant dispersing module comprises a blower, heater, vaporization chamber and liquid decontaminant container.

7. The decontamination unit of claim 6 wherein the decontaminant dispersing module further comprises a process air inlet, decontaminant air mixture outlet, and a compressed air inlet.

8. The decontamination unit of claim 1 wherein the area to be decontaminated comprises an enclosure with an internal volume in the range from about 10 to about 10,000 cubic meters.

9. The decontamination unit of claim 1 wherein the area to be decontaminated comprises a multi-room facility, the decontamination unit being adapted to provide at least one decontaminant dispersing module in each room of the multi-room facility.

10. The decontamination unit of claim 1 wherein the internal combustion engine comprises a compression ignition engine or a spark ignition engine.

11. The decontamination unit of claim 1 wherein the internal combustion engine comprises a two-cycle engine, four-cycle engine, rotary engine, or gas turbine engine.

12. The decontamination unit of claim 1 wherein the internal combustion engine is adapted to be operated using diesel fuel, gasoline, petroleum gas, propane gas, natural gas, liquefied petroleum gas, hydrogen gas, biofuel, or a mixture of two or more thereof.

13. The decontamination unit of claim 1 wherein the internal combustion engine comprises an exhaust gas system, the exhaust gas system comprising an exhaust gas heat exchanger adapted to transfer heat from exhaust gas to coolant flowing from the internal combustion engine to the heat recovery coil.

14. The decontamination unit of claim 1 wherein the electric generator has a power rating in the range from about 30 to about 150 kVA.

15. The decontamination unit of claim 1 wherein the condensing unit has a cooling capacity in the range from about 5 to about 25 tons of refrigeration.

16. The decontamination unit of claim 1 wherein the power generating unit, air handling unit and/or decontaminant dispersing module are ruggedized.

17. A decontamination process, comprising:
operating an internal combustion engine, the internal combustion engine providing power to an electric generator, the internal combustion engine generating heat and being cooled using a coolant, the internal combustion engine and electric generator positioned in a power generating unit;
flowing process air containing water vapor using a blower past an evaporator coil to condense water vapor and separate it from the process air, the evaporator coil being part of a condensing unit, the electric generator providing power to operate the condensing unit and the blower;
flowing coolant from the internal combustion engine to a heat recovery coil;
flowing the process air from the evaporator coil using the blower past the heat recovery coil to heat the process air, the heat recovery coil, evaporator coil and blower positioned in an air handling unit;
mixing the process air with a decontaminant to form a decontaminant air mixture in a decontaminant dispersing module; and
flowing the decontaminant air mixture in an enclosure to be decontaminated.

18. The process of claim 17 wherein an exhaust gas is produced by the internal combustion engine, and heat from the exhaust gas is transferred to the coolant flowing from the internal combustion engine to the heat recovery coil.

19. The process of claim 17 wherein the decontaminant comprises a peracid, peroxide, hypochlorite, ozone, or a mixture of two or more thereof.

20. The process of claim 19 wherein the decontaminant further comprises an alkaline gas.

21. The process of claim 17 wherein the decontaminant comprises hydrogen peroxide.

22. The process of claim 21 wherein the decontaminant further comprises a solvent.

23. The process of claim 17 wherein the decontaminant comprises vaporous hydrogen peroxide and ammonia.

24. The process of claim 17 wherein the enclosure to be decontaminated is contaminated with one or more chemical, biological, radiological and/or nuclear warfare agents.

25. The process of claim 17 wherein the enclosure to be decontaminated is contaminated with one or more bacterial spores, vegetative bacteria, viruses, molds and/or fungi.

26. The process of claim 17 wherein the enclosure to be decontaminated is contaminated with one or more pathogenic chemical agents.

27. The process of claim 17 wherein the internal combustion engine, electric generator, condensing unit, evaporator coil and/or heat recovery coil are ruggedized.

28. The process of claim 17 wherein the decontamination process comprises a dry process characterized by the absence of condensate formation on the surface of the enclosure to be decontaminated.

29. The process of claim 17 wherein the decontamination process comprises a wet process characterized by the formation of condensate on the surface of the enclosure to be decontaminated.

30. The process of claim 29 wherein the condensate comprises hydrogen peroxide.

* * * * *